United States Patent [19]

Hatfield

[11] 4,175,076
[45] Nov. 20, 1979

[54] AZETIDINONE MERCURY SULFIDES AND PROCESS THEREFOR

[75] Inventor: Lowell D. Hatfield, Bargersville, Ind.

[73] Assignee: Eli Lilly and Company, Indianapolis, Ind.

[21] Appl. No.: 853,064

[22] Filed: Nov. 21, 1977

[51] Int. Cl.² .......................................... C07D 205/08
[52] U.S. Cl. ............................ 260/239 A; 260/239.1; 260/326.22; 544/30
[58] Field of Search ....................... 260/239 A, 326.22

[56] References Cited

U.S. PATENT DOCUMENTS 4,029,645  6/1977  Slusarchyk et al. .......... 260/239 AL
4,130,557  12/1978  Hamashima ................... 260/239 A

FOREIGN PATENT DOCUMENTS 7600950  1/1976  Netherlands.

OTHER PUBLICATIONS

Kamai et al., Chem. Abs. 76, 45351a.

Primary Examiner—Mark L. Berch
Attorney, Agent, or Firm—Steven R. Lammert; Arthur R. Whale

[57] ABSTRACT

Novel azetidinone mercury sulfides are prepared by the reaction of penicillin derived thiazolineazetidinones with a mercuric halide in the presence of an alcohol or glycol. They are useful intermediates in the preparation of cephalosporin compounds.

10 Claims, No Drawings

AZETIDINONE MERCURY SULFIDES AND PROCESS THEREFOR

BACKGROUND

Common to the bicyclic structures of both penicillins and cephalosporins is the β-lactam or azetidinone moiety. Because of the significance which microbioligists have attributed to the presence of the β-lactam entity in the structure of these active antibiotic compounds, many chemists in search of new antibiotic compounds have used the β-lactam ring system as a nucleus from which to carry out their research. Of course, there have been many new β-lactam intermediates, both monocyclic and bicyclic, resulting from such research efforts and from similar research efforts directed to penicillin-cephalosporin conversions. Many such intermediates have been derived from penicillins and cephalosporins; others have been prepared by totally synthetic means.

This invention relates to certain monocyclic azetidinone mercury sulfide intermediates, useful in the synthesis of cephalosporins derivatives, and to a method of preparation of such intermediates from penicillin sulfoxide derived bicyclic thiazolineazetidinones.

SUMMARY OF THE INVENTION

This invention is directed to azetidinone compounds of the formula

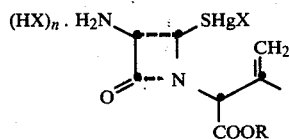

and to a process for their preparation by the reaction of known penicillin derived thiazolineazetidinones with mercuric halides in the presence of an alcohol or a glycol.

DETAILED DESCRIPTION OF THE INVENTION

As delineated hereinabove the novel azetidinone compounds of this invention have the formula

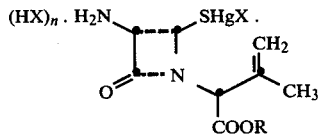

wherein n is 0 or 1, X is chloro or bromo, R is hydrogen or a carboxylic acid ester protecting group. These compounds are prepared in the process of this invention by reacting a compound of the formula

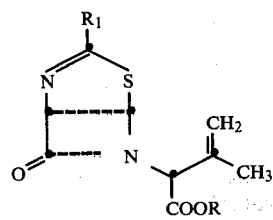

with about 1.0 to about 1.2 equivalents of a mercuric halide of the formula $HgX_2$ in an inert organic solvent in the presence of at least about an equivalent amount of a $C_1-C_8$ primary or secondary alcohol or $C_1-C_8$ diol wherein in the above formula X is chloro or bromo, R is hydrogen or a carboxylic acid ester protecting group and $R_1$ is (a) $C_1-C_4$ alkyl, or halo-$C_1-C_4$ alkyl;

(b) benzyloxy, 4-nitrobenzyloxy, 2,2,2-trichloroethoxy, tert-butoxy, benzhydryloxy, 4-methoxybenzyloxy;

(c) the group $R_2$ wherein $R_2$ is 1,4-cyclohexadienyl, phenyl or phenyl substituted with 1 or 2 groups selected from the group consisting of chloro, bromo, iodo, hydroxy, $C_1-C_4$ alkoxy, $C_1-C_4$ alkyl, nitro, cyano, or trifluoromethyl; and (d) an arylalkyl group of the formula

wherein $R_2$ is as defined above and m is 1 or 0; or (e) a heteroarylmethyl group of the formula $R_3CH_2-$ wherein $R_3$ is 2-thienyl, 3-thienyl, 2-furyl, 2-thiazolyl, 5-tetrazolyl, 1-tetrazolyl or 4-isoxazolyl.

In the foregoing definition of the process and compounds of the present invention the term "$C_1-C_4$ alkyl" refers to methyl, ethyl, isopropyl, n-propyl, isobutyl, n-butyl and like lower alkyl groups. Exemplary of $C_1-C_4$ alkoxy are methoxy, ethoxy, isopropoxy, tert-butoxy, n-propoxy and like groups. "Halo-$C_1-C_4$ alkyl" refers to chloromethyl, bromomethyl, iodoethyl, 2-chloropropyl, 3-bromopropyl, 2-iodobutyl, 3-chlorobutyl, 1-chlorobutyl and like groups.

The term carboxylic acid ester protecting group has reference to those commonly employed ester groups used to block or protect the carboxylic acid funtionality while reactions involving other functional sites of the compound are carried out. Such protecting groups are noted for their ease of cleavage from the carboxy group by hydrolytic or hydrogenolytic methods to provide the corresponding carboxylic acid. Many such groups and their properties are well known in the art. Examples of carboxylic acid ester protecting groups are tert-butyl, 1-methylcyclohexyl, benzyl, 4-methoxybenzyl, $C_2-C_6$ alkanoyloxymethyl, 2-iodoethyl, 2-bromoethyl, 4-nitrobenzyl, diphenylmethyl (benzhydryl), phenacyl, 4-halophenacyl, dimethylallyl, 2,2,2-trichloroethyl, succinimidomethyl and $C_1-C_3$ alkoxymethyl. Other known carboxylic acid protecting groups are described by E. Haslam in "Protective Groups in Organic Chemistry", J. F. W. McOmie, Ed., Plenum Press, New York, New York, 1973, Chapter 5. The nature of such protecting groups is not critical so long as the particular group employed is stable under the relatively mild conditions of the present process. Preferred carboxylic acid protecting groups are tert-butyl, 4-methoxybenzyl, 4-nitrobenzyl, benzhydryl and 2,2,2-trichloroethyl.

Representative of the group $R_1$ when $R_2$ is substituted phenyl are 4-chlorophenyl, 2-chlorophenyl, 3-methyl-4-bromophenyl, 4-alkoxy-2-chlorophenyl, 4-hydroxyphenyl, 3-nitrophenyl, 4-cyanophenyl, 4-isopropoxyphenyl, 4-trifluoromethylphenyl, 3-methyl-4-n-butoxyphenyl, 4-nitro-3-chlorophenyl, and 2-hydroxy-4-methoxyphenyl.

Exemplary of $R_1$ when $R_1$ is a group of the formula $R_2-(O)_mCH_2-$ are benzyl, phenoxymethyl, 1,4-cyclohexadienylmethyl, 4-chlorophenoxymethyl, 2-methyl-4-hydroxybenzyl, 3-nitrobenzyl, 2-bromophenoxymethyl, 4-trifluoromethylbenzyl, 3,4-dimethoxybenzyl, 2,4-dichlorophenoxymethyl, and 3-cyano-4-ethoxybenzyl.

The thiazolineazetidinone starting materials for the preparation of the compounds of the present invention by the present process are known compounds derived from penicillin sulfoxide esters by their reaction at elevated temperatures with trimethylphosphite. The preparation of these starting materials is detailed in U.S. Pat. No. 3,705,892 issued Dec. 12, 1972. Preferred starting materials are those derived from 6-phenylacetamido and 6-phenoxyacetamido penicillin sulfoxide esters.

Typically the process of this invention is carried out simply by stirring a mixture of the substrate thiazolineazetidinone, the mercuric halide and the alcohol or glycol in an inert organic solvent at room temperature. The temperature at which the present process is carried out is not critical. Higher or lower temperatures can be employed but without advantage over the preferred room temperature (about 20° to about 30° C.) reactions.

Any of a wide variety of inert organic solvents may be employed as the medium for the present process. By "inert organic solvent" is meant an organic solvent which, under the conditions of the process does not enter into any appreciable reaction with either the reactants or the products. Suitable solvents include for example, aromatic hydrocarbons, such as benzene, toluene, xylene, chlorobenzene, nitrobenzene and the like; halogenated aliphatic hydrocarbons, such as chloroform, methylene chloride, carbon tetrachloride, 1,2-dichloroethane (ethylene chloride), 1,1,2-trichloroethane, 1,1-dibromo-2-chloroethane; esters such as ethyl acetate and methyl acetate; ethers such as dioxane, tetrahydrofuran, diethyl ether, diisopropyl ether and 1,2-dimethoxyethane; nitriles such as acetonitrile or proprionitrile; and other solvents, including among others, nitromethane, dimethylformamide, dimethylacetamide and acetone. Preferred solvents are the halogenated aliphatic hydrocarbons. Most preferred is methylene chloride.

Suitable mercuric halide reagents for the present process are mercuric chloride and mercuric bromide. Mercuric chloride is preferred.

When mercuric chloride is employed the products of the present process are azetidinonethio mercury chloride hydrochlorides of the present invention. Similarly when mercuric bromide is employed in the present process the products are azetidinonethio mercury bromide hydrobromide compounds of the present invention.

To ensure completion of the reaction at least a stoichiometric (mole per mole) amount of the mercuric halide is employed. Using less than 1 equivalent of this reagent will result in lower yields of the product and will leave a portion of the starting material unreacted. Typically about 1.0 to about 1.2 equivalents of mercuric halide is employed for each mole of thiazolineazetidinone starting material.

As mentioned hereinabove it is necessary that the reaction be carried out in the presence of an alcohol or a diol (glycol). A primary or secondary $C_1$–$C_8$ alcohol or $C_1$–$C_8$ diol is typically employed. Suitable primary $C_1$–$C_8$ alcohols are methanol, ethanol, n-propanol, n-butanol, isobutanol, n-pentanol, benzyl alcohol, isooctyl alcohol and like lower alcohols. Suitable secondary alcohols are isopropanol, sec-butanol, 2-hydroxypentane, cyclohexanol, 2-hydroxyoctane and like secondary alcohols. Representative of diols which may be employed in the present process are ethylene glycol, propylene glycol, 2,2-dimethyl-1,3-propandiol, 1,2-butandiol, 1,3-butandiol, 1,4-butandiol, 2-butene-1,4-diol, 1,2-cyclohexandiol and 1,3-cyclohexandiol. Since product yields are typically higher when diols rather than alcohols are employed in the present process, diols are preferred.

The alcohol or diol employed should be present in at least a stoichiometric (mole per mole) amount. Preferably about 2 to about 10 moles of alcohol or diol are employed for each mole of thiazolineazetidinone starting material. A greater excess of alcohol or diol can be employed, but without advantage.

Although it is readily apparent from the foregoing description, it should be noted that the structure of the products from the present process is independent of the nature of the alcohol or diol employed.

The reaction times for the present process are not critical. The reaction begins when the reagents are combined and thereafter proceeds at varying rates depending on the various reaction parameters such as the nature of the substrate, reaction temperature, and the particular solvent employed. The progress of the reaction can be followed by comparative thin-layer chromatography. Reaction times generally range from about 30 minutes to about 12 hours. Typically the reaction is allowed to proceed for about 3 to about 6 hours.

In a specific example of the present process a compound of the present invention of the formula

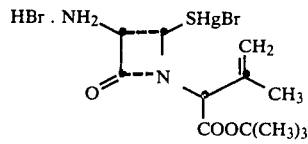

is prepared by adding 2.2 equivalents of mercuric bromide to a solution of 2 equivalents of a thiazolineazetidinone of the formula

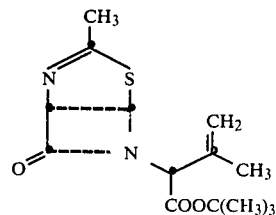

and 10 equivalents of sec-butanol in 1,2-dichloroethane at room temperature. The corresponding mercuric chloride hydrochloride is obtained when mercuric chloride is employed.

Representative of the compounds prepared by the process of the present invention are

[[1-[1-(benzhydryloxycarbonyl)-2-methylprop-2-enyl]-3-amino-4-oxo-2-azetidinyl]thio]mercury hydrochloride,

[[1-[1-(1-methylcyclohexyloxycarbonyl)-2-methylprop-2-enyl]-3-amino-4-oxo-2-azetidinyl]thio]mercury chloride hydrochloride,

[[1-[1-(phenacyloxycarbonyl)-2-methyl-2-methylprop-2-enyl]-3-amino-4-oxo-2-azetidinyl]thio]mercury chloride hydrochloride,

[[1-[1-(2,2,2-trichlorethoxycarbonyl)-2-methylprop-2-enyl]-3-amino-4-oxo-2-azetidinyl]thio]mercury bromide hydrobromide,

[[1-[1-(4-nitrobenzyloxycarbonyl)-2-methylprop-2-enyl]-3-amino-4-oxo-2-azetidinyl]thio]mercury bromide hydrobromide,

[[1-[1-benzyloxycarbonyl-2-methylprop-2-enyl]-3-amino-4-oxo-2-azetidinyl]thio]mercury chloride hydrochloride,

[[1-[1-(4-methoxybenzyl)-2-methylprop-2-enyl]-3-amino-4-oxo-2-azetidinyl]thio]mercury chloride hydrochloride, and

[[1-[1-(2-iodoethoxycarbonyl)-2-methylprop-2-enyl]-3-amino-4-oxo-2-azetidinyl]thio]mercury chloride hydrochloride.

The products produced in accordance with the process of this invention can be isolated and purified by employing conventional laboratory techniques. These include filtration, crystallization, recrystallization, trituration and chromatography. Usually the product crystallizes in the reaction mixture and is isolated simply by filtration.

The compounds of the present invention are useful as intermediates in the preparation of known cephalosporin antibiotic compounds. They react with excess chlorine in an inert organic solvent such as chloroform, methylene chloride, ethyl acetate or dimethylformamide to provide a mixture of the corresponding 6-amino-2-chloromethyl-2-methylpenam-3-carboxylate and 7-amino-3-chloro-3-methylcepham-4-carboxylate:

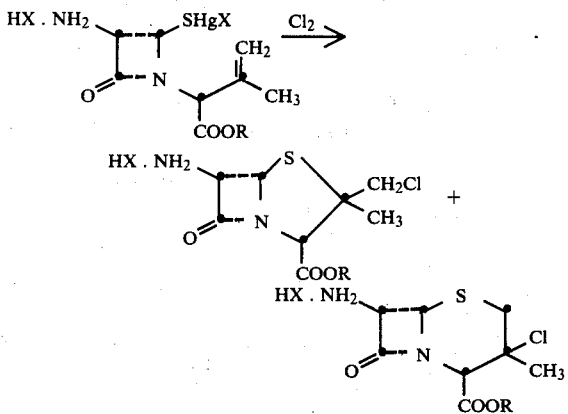

The mixture can be acylated by conventional acylation procedures and separated using, for example, column chromatography to provide the corresponding 6-acylamino-3-chloro-3-methylcepham-4-carboxylate. Dehydrohalogenation of the 3-chloro-3-methylcepham derivatives is accomplished by treatment with an organic base such as pyridine or triethylamine in methylene chloride to provide the corresponding desacetoxycephalosporins of the formula

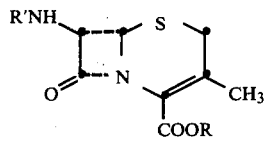

wherein R' is an acyl group derived from a carboxylic acid and R is hydrogen or a carboxylic acid ester protecting group. Cleavage of the ester protecting group R can be achieved using well known methods. Thus, where the carboxylic acid protecting group is benzhydryl, tert-butyl, 4-methoxybenzyl or 1-methylcyclohexyl, deesterification is accomplished by treatment of the ester with an acid such as trifluroacetic acid, in the presence of anisole. The 2-iodoethyl, 2-bromoethyl, 4-nitrobenzyl and 2,2,2-trichloroethyl protecting groups are removed with zinc and an acid such as acetic or hydrochloric acid. The 4-nitrobenzyl protecting group can also be removed by hydrogenation in the presence of palladium, platinum, rhodium or a compound thereof, is suspension or on a carrier such as barium sulfate, carbon, alumina or the like. Other carboxy protecting groups are removed by hydrolysis under basic conditions.

The antibiotic activity of the resulting cephem acids has been well documented. One such cephem acid is cephalexin (R' in the above formula

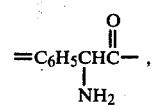

R=H), a compound of substantial clinical and commercial significance.

The following examples are provided to further illustrate this invention.

EXAMPLE 1

[[1-[1-(4-Nitrobenzyloxycarbonyl)-2-methylprop-2-enyl]-3-amino-4-oxo-2-azetidinyl]thio]mercury chloride hydrochloride To a suspension of 35 g (130 mmol) of mercuric chloride in 603 ml of methylene chloride was added 56.22 g (120 mmol) of 2-phenoxymethyl-7-[1-(4-nitrobenzyloxycarbonyl)-2-methylprop-2-enyl]-1,3,6-diazabicyclo[3.2.0]hept-2-en-5-one. Then 67 ml (53.6 g, 720 mmol) of isobutanol was added. The reaction mixture was allowed to stir at room temperature for 5.5 hours. The product, which crystallized in the reaction mixture, was filtered, washed with methylene chloride and dried. Yield—40.45 g (54%): nmr (DMSO-$d_6$) δ 1.86 (bs, 3, $CH_3$), 4.83 (1, d, J=4 Hz, $C_2$—H), 4.96 (s, 1, —C$\underline{H}$COO—), 5.1 (bs, 2, =$CH_2$), 5.40 (s, 2, ester $CH_2$), 5.76 (1, d, J=4 Hz, $C_3$—H), 7.4–8.3 (q, 4, ArH), and 8.76 (bs, 2, N$\underline{H}_2$—HCl).

EXAMPLE 2

[[1-[1-(4-Nitrobenzyloxycarbonyl)-2-methylprop-2-enyl]-3-amino-4-oxo-2-azetidinyl]thio]mercury chloride hydrochloride (A) A mixture of 9.2 g (20 mmol) of 2-phenoxymethyl-7-[1-(4-nitrobenzyloxycarbonyl)-2-methylprop-2-enyl]-1,3,6-diazabicyclo-[3.2.0]hept-2-en-5-one, 5.8 g (21.5 mmol) of mercuric chloride, 100 ml of methylene chloride, and 18.75 ml (120 mmol) of 2-ethylhexanol was stirred 5 hours at room temperature. The title product, which crystallized from the reaction mixture, was filtered, washed with methylene chloride and dried. Yield 8.14 g (65%).

Several experiments were performed in accordance with the procedure described above except that other alcohols and diols were substituted for the 2-ethylhexanol. The following paragraphs describe the nature and amount of the substituted alcohol or diol and the yield of crystalline product obtained:

(B) 1,3-Propandiol (4.35 ml, 60 mmol); yield—11.41 g (91.3%)

(C) 1,3-Butandiol (5.36 ml, 60 mmol); yield—9.69 g. (77.5%)

(D) 2,2-Dimethyl-1,3-propandiol (60 mmol); yield—12.27 g (98%).

(E) Propyleneglycol (1,2-propandiol) (60 mmol); yield—11.30 g (90.4%).

(F) Methanol (60 mmol); yield—8.10 g (64.8%).

(G) n-Butanol (60 mmol); yield—7.22 g (57.8%).

EXAMPLE 3

[[1-[1-(2,2,2-Trichloroethoxycarbonyl)-2-methylprop-2-enyl]-3-amino-4-oxo-2-azetidinyl]thio]mercury chloride hydrochloride Mercuric chloride 2.9 g (10.7 mmol) was added to a solution of 4.6 g (10 mmol) of 2-phenoxymethyl-7-[1-(2,2,2-trichloroethoxycarbonyl)-2-methylprop-2-enyl]-1,3,6-diazabicyclo[3.2.0]hept-2-en-3-one in a mixture of 50 ml methylene chloride, 10 ml of methanol and 5 ml water. The reaction mixture was stirred overnight at room temperature. The crystalline product was filtered from the reaction mixture, washed with methanol and dried in vacuo at 50°. Yield—3.7 g (63%); nmr (DMSO-d$_6$) δ 1.9 (bs, 3, CH$_3$), 4.73 (d, 1, J=4 Hz, C$_2$—H), 4.95 (bs, 2), 5.0 (s, 1), 5.76 (d, 1, J=4 Hz, C$_3$—H), 8.73 (bs, 2, —NH$_2$.HCl).

I claim:

1. A process for preparing a compound of the formula

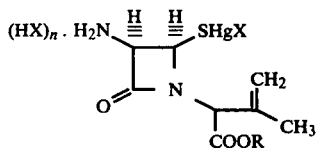

by reacting a compound of the formula

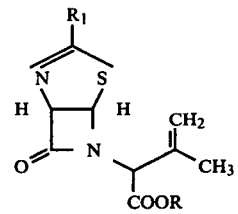

with about 1.0 to about 1.2 equivalents of a mercuric halide of the formula HgX$_2$ in an inert organic solvent in the presence of at least about an equivalent amount of a C$_1$ to C$_8$ primary or secondary alcohol or C$_1$–C$_8$ diol wherein in the above formulas n is 1 or 0, X is chloro or bromo, R is hydrogen or a carboxylic acid ester protecting group and R$_1$ is
  (a) C$_1$–C$_4$ alkyl or halo-C$_1$–C$_4$ alkyl;
  (b) benzyloxy, 4-nitrobenzyloxy, 2,2,2-trichloroethoxy, tert-butoxy, benzhydryloxy, 4-methoxybenzyloxy;
  (c) the group R$_2$ wherein R$_2$ is 1,4-cyclohexadienyl, phenyl or phenyl substituted with 1 or 2 substituents selected from the group consisting of chloro, bromo, iodo, hydroxy, nitro, cyano, trifluoromethyl, C$_1$–C$_4$ alkyl or C$_1$–C$_4$ alkoxy;
  (d) an arylalkyl group of the formula R$_2$—(O)$_m$—CH$_2$— wherein R$_2$ is as defined above and m is 0 or 1; or
  (e) a heteroarylmethyl group of the formula

R$_3$CH$_2$— wherein R$_3$ is 2-thienyl, 3-thienyl, 2-furyl, 2-thiazolyl, 5-tetrazolyl, 1-tetrazolyl, or 4-isoxazolyl.

2. The process of claim 1 wherein R is a carboxylic acid ester protecting group.

3. The process of claim 2 wherein the mercuric halide is mercuric bromide.

4. The process of claim 2 wherein the mercuric halide is mercuric chloride.

5. The process of claim 4 wherein the inert organic solvent is a halogenated aliphatic hydrocarbon.

6. The process of claim 4 wherein the inert organic solvent is methylene chloride.

7. The process of claim 4 wherein about 2 to about 10 equivalents of a C$_1$–C$_8$ diol is employed.

8. The process of claim 7 wherein the diol is 1,3-propandiol, 1,3-butandiol, 2,2-dimethyl-1,3-propandiol or 1,2-propandiol.

9. The process of claim 4 wherein R$_1$ is benzyl or phenoxymethyl.

10. The process of claim 4 wherein R is tert-butyl, 4-methoxybenzyl, 4-nitrobenzyl, benzhydryl and 2,2,2-trichloroethyl.

* * * * *